United States Patent [19]
Koch

[11] Patent Number: 6,052,610
[45] Date of Patent: Apr. 18, 2000

[54] MAGNETIC CATHETER TRACKER AND METHOD THEREFOR

[75] Inventor: Roger Hilsen Koch, Amawalk, N.Y.

[73] Assignee: International Business Machines Corporation, Armonk, N.Y.

[21] Appl. No.: 09/004,834

[22] Filed: Jan. 9, 1998

[51] Int. Cl.[7] ...................................................... A61B 5/05
[52] U.S. Cl. ...................... 600/424; 324/207.11; 324/260
[58] Field of Search .................... 600/407, 424; 128/899; 324/244, 260, 246, 247, 256, 259, 261, 207.11, 207.13, 207.17

[56] References Cited

U.S. PATENT DOCUMENTS

| | | | |
|---|---|---|---|
| 5,425,367 | 6/1995 | Shapiro et al. | 128/653.1 |
| 5,592,939 | 1/1997 | Martinelli et al. | 128/653.1 |
| 5,622,169 | 4/1997 | Golden et al. | 600/424 |
| 5,645,065 | 7/1997 | Shapiro et al. | 128/653.1 |
| 5,762,064 | 6/1998 | Polvani | 600/424 |
| 5,762,599 | 6/1998 | Sohn | 600/30 |
| 5,775,322 | 7/1998 | Silverstein et al. | 128/899 |
| 5,879,297 | 3/1999 | Haynor et al. | 600/424 |
| 5,902,238 | 5/1999 | Golden et al. | 600/424 |

*Primary Examiner*—Brian L. Casler
*Attorney, Agent, or Firm*—Whitham, Curtis & Whitham

[57] ABSTRACT

A method, apparatus, and system for tracking an object within a volume, includes coupling a rotating magnetic dipole to the object, measuring the magnetic fields either remotely, on the surface of, or exterior to the volume, to produce measurements; and based on the measurements, determining the position and the orientation of the magnetic dipole, thereby to determine a position and orientation of the object.

10 Claims, 3 Drawing Sheets

MAGNETIC CATHETER TRACKER AND METHOD THEREFOR

BACKGROUND OF THE INVENTION

The present invention generally relates to a system, apparatus and method for tracking an object in a body or region, and more particularly to a system, apparatus and method for determining the position and orientation of a probe, such as a catheter, in a volume such as a human body by tracking the position of a rotating magnet or oscillating magnetic dipole that is placed in or on the probe or catheter.

DESCRIPTION OF THE RELATED ART

Generally, with the existing technology and techniques, it has been very difficult to locate in three dimensions an object in a three-dimensional volume. Most conventional systems use separate two-dimensional images of an area of interest. However, the exact relative positions of the separate images are unknown, because the accuracy of the conventional methods for determining the location of the images is poor. Hence, finding an object in a three-dimensional volume, such as a human body, has been difficult, if not impossible, with the conventional techniques.

In many surgical procedures, physicians must insert probes (e.g., catheters) into the human body, and later must detect the position of the catheters for additional treatment, investigation, manipulation, removal from the body, etc.

Typically, the positions of the catheters are measured using a simple x-ray imaging system such as a fluoroscope or the like. However, this system images primarily in two dimensions (e.g., as shown in FIG. 2) and is incapable of indicating the exact angular orientation of the catheter around its long axis. Precise quantitative information of the position of the catheter in the three spatial dimensions and the three orientation angles would be of great benefit.

For example, when a physician uses an ultrasonic transducer mounted on the rotating tip of a catheter imager to image the plaque in a person's arteries near or around the heart, the physician receives a series of two-dimensional images from the ultrasonic imager as the catheter is pulled through the blood vessels. However, the exact relative positions of the separate images are unknown, because the accuracy of the present methods for determining the location of the images is poor and incapable of measuring the orientation angles of the catheter. In any application where catheters or instruments must be placed into or next to the human body in a medical procedure, precise quantitative information of the precise location and angle of each probe would be of great value.

Moreover, extending beyond the problem of tracking a catheter in the human body, there are many situations where measuring the exact position and orientation of an object using remote sensors would be highly beneficial.

SUMMARY OF THE INVENTION

In view of the foregoing problems of the conventional systems and methods as first recognized by the present inventor, an object of the present invention is to provide a system, apparatus and method for accurately tracking a probe (e.g., catheter) in a three-dimensional continuum by either utilizing a preexisting rotating motion of the probe (or by adding a rotating motion to the same), and attaching a small permanent magnet to the probe.

Another object is to provide a system, apparatus and method for accurately tracking the position a rotating ultrasonic catheter in a human body by using magnetic tracking.

In a first aspect of the present invention, an extremely small (e.g., approximately 1–2 mm$^2$) but powerful (e.g., on the order of about $10^{-2}$ Amp·m$^2$) rare-earth magnet is positioned on a probe or the tip of a catheter.

With the present invention, the tip of the probe or catheter must rotate (or be made to rotate) around some axis. Such an alteration of the probe or catheter is inexpensive and relatively simple on those probes or catheters that already have such a rotating motion. Rotating motion could be added to those probes or catheters that do not already rotate (e.g., through a motor or the like), which again would be an inexpensive and simple retro-fit in many situations.

When the probe or catheter is in the volume or body of interest, magnetic field sensors placed around the volume, or next to the body, record the magnetic fields generated by the rotating magnet on the probe or catheter.

Using the outputs of the magnetic field sensors, mathematical algorithms and a computer/processor can determine the exact position and orientation of the magnet, and hence the exact position and orientation of the probe or catheter. This allows exact positional information to be recorded as the probe or catheter is moved.

For an ultrasonic catheter, the computer constructs a three-dimensional image of all the separate two-dimensional ultrasonic images obtained from the imager.

Thus, with the present invention, a magnet is attached to the tip of a catheter, and when this catheter is placed inside the body (e.g., blood vessels), magnetic field measurements exterior to the body can accurately determine the position and orientation of the magnet, and, hence the position and orientation of the catheter.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1A:
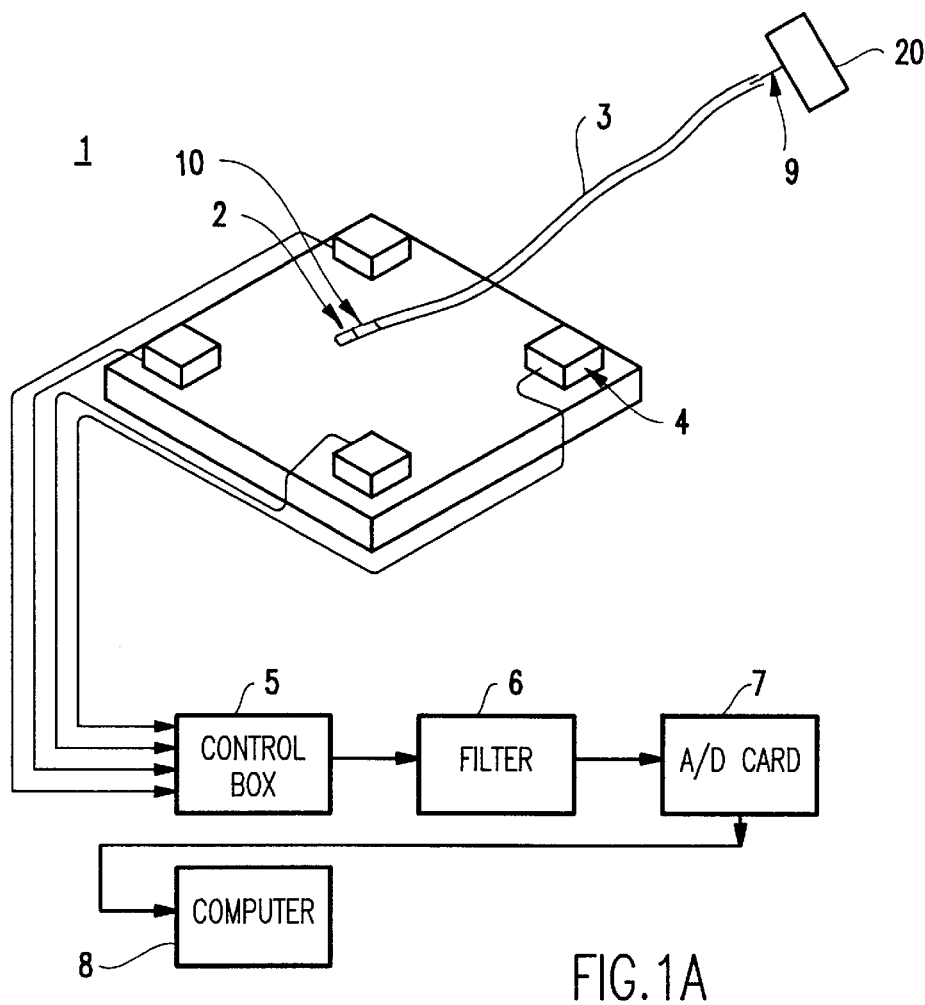
FIG. 1A is a block diagram illustrating a system for tracking an object according to the present invention.

Referring now to the drawings, and more particularly to FIG. 1A, there is shown a block diagram of the system for tracking an object (e.g., such as a catheter) in a body (e.g., such as the human body).

As shown in FIG. 1A, a system 1 is provided for tracking a magnetic dipole 2 attached to a first end (e.g., tip) of an elongated probe (e.g., a catheter in the exemplary application) 3. For example, the magnetic dipole preferably includes a rotating permanent magnet. The magnet is preferably extremely small (e.g., approximately 1–2 mm$^2$) but powerful (e.g., on the order of about $10^{-2}$ Amp·m$^2$) rare-earth magnet is positioned on a probe. While not as preferred for the present invention as the rotating rare earth magnet, it is conceivable that an electromagnet with a constant current, an electromagnet with an alternating current applied thereto, or the like could be used with suitable modifications, as would be known by one of ordinary skill in the art taking the present specification as a whole.

A second end of the catheter 3 is for insertion into a body of interest (e.g., a human body). The catheter 3 may have any diameter. For example, in one implementation, the catheter 3 has an outer diameter of 1 mm.

As shown in FIG. 1A, the present invention measures the magnetic field at a plurality (e.g., two or more) of positions. The measurements are made with a magnetic sensing device (e.g., magnetometer) 4, such as a SQUID, a flux gate, a magneto-resistive sensor, a hall probe, or the like. Preferably, a 3-axes magnetometer is used as the magnetic sensing device. However, configurations are possible with 1-, 2-, or 3-axis (or more) sensors. However, a sensor having 3 axes is preferred, with a 6-coordinate display being shown in FIG. 1B.

In the implementation shown in FIG. 1A, the magnetometers 4 are preferably mounted in the corners of a substrate or in other suitable positions based on operating characteristics and designer constraints.

Figure 1B:
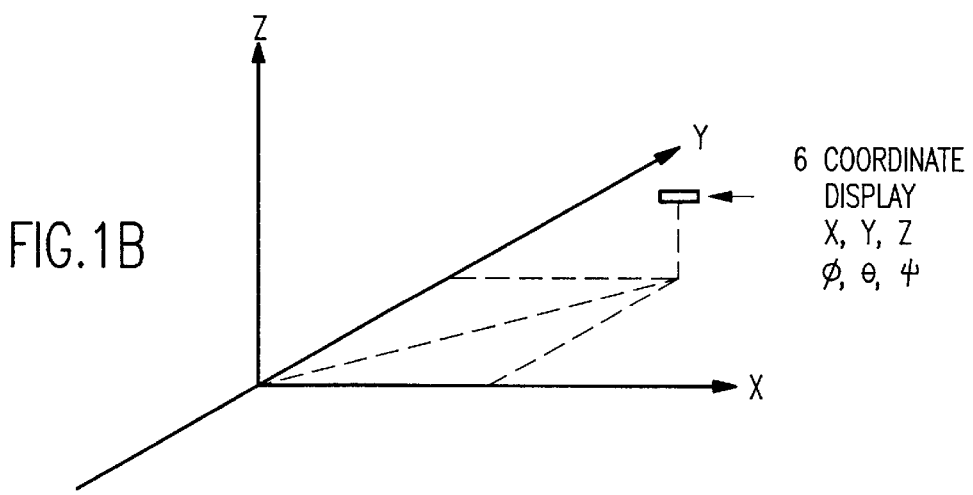
FIG. 1B illustrates a coordinate system for use with the present invention.

It is noted that while four magnetometers are shown in FIG. 1B, only two magnetometers are needed to localize the rotating magnet 2. Hence, any configuration of stationary magnetic sensors could be used. An algorithm used by the present invention allows an arbitrary orientation, and/or positioning, but requires at least two magnetometers to be placed at different positions. As mentioned above, the magnetometers preferably comprise a three-axes magnetometer.

The outputs of the magnetometers 4, representing the values of the magnetic fields, are provided to a control box 5 for operating the magnetometers. The control box 5 is available commercially, or alternatively may be constructed by one of ordinary skill in the art by assembling standard electronics for operating the magnetometers.

It is noted that there are three outputs for each magnetometer 4 (although only one is shown for convenience and brevity in FIG. 1A). In other words, in the system as shown in FIG. 1A, there are 12 outputs total, since there are provided four magnetometers 4.

The outputs of the control box 5 are filtered by filters 6. Specifically, a filter box 6 including a plurality of filters is for providing a band pass around the rotational frequency of the magnet, which helps reduce environmental noise signals from affecting the output of the tracker.

The output of the control box 5 represents the oscillating magnetic field that each of the magnetic sensors 4 is recording.

Filters 6 preferably comprise a band-pass filter at the rotational frequency of the magnet. Preferably, there is a filter 6 provided corresponding to each magnetic sensor 4. Also, there can be a gain in the filter box electronics (e.g., typically a gain of about 10 to 100, but of course any gain can be provided depending upon the designer's constraints and requirements).

Thereafter, the output of the filters 6 is digitized by an analog-to-digital (A/D) converter 7, in order to input digital values representing the magnetic fields into a computer (processor) 8.

It is noted that a motor 20 is preferably provided for rotating the magnet 2. The motor 20 also provides an AC reference synchronization signal (e.g., for synchronization with the magnet) to the A/D converter 7. The motor 20 is provided on one end of the probe (catheter), and the magnet is provided on the other end of the probe, as shown in FIG. 1B.

Figure 2:
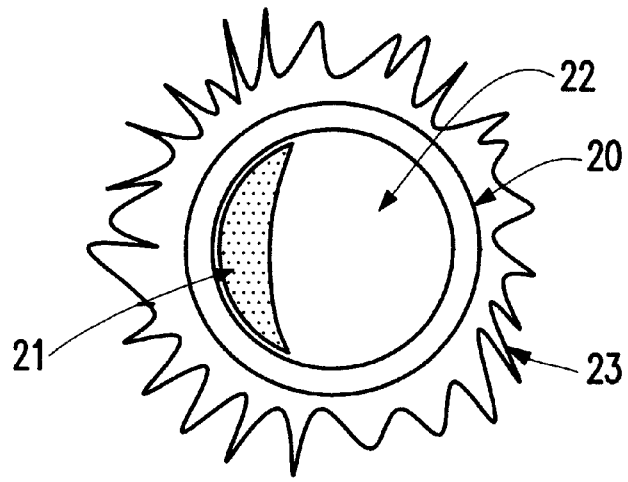
FIG. 2 illustrates a schematic, two-dimensional image of an artery from an ultrasonic imager.

As mentioned above, a schematic two-dimensional image of an artery wall 20 from an ultrasonic imager (e.g., 10 as shown in FIG. 1) is shown in FIG. 2. Such a two-dimensional schematic is similar to that provided by the conventional systems and techniques. The artery wall includes plaque 21 formed thereon, thereby reducing the cross-sectional area of the artery for carrying blood 22. Heart tissue 23 is shown surrounding the artery in this exemplary application.

Figure 3:
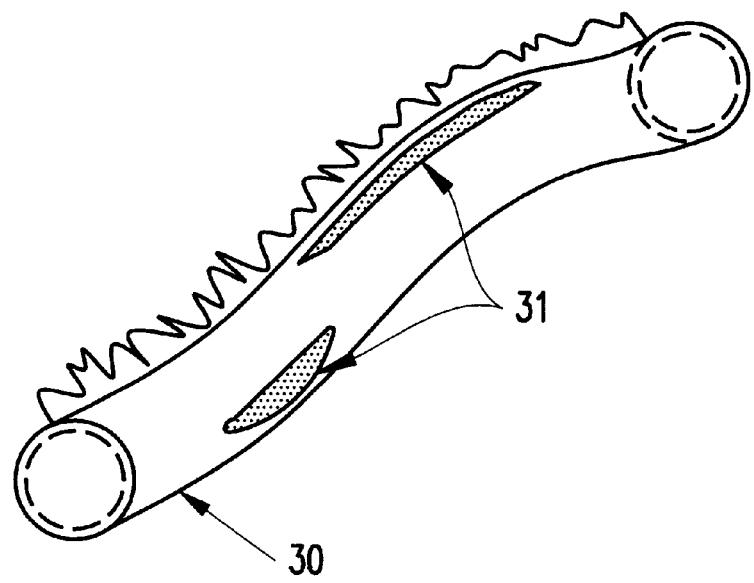
FIG. 3 illustrates a schematic, three-dimensional image using the system and method according to the present invention.

In contrast to the schematic image of FIG. 2, a schematic three-dimensional image using a rotating magnetic tracking (e.g., made possible by the rotating shaft 9 coupled to the catheter 3 as shown in FIG. 1A) according to the present invention is shown in FIG. 3. As shown, the positioning of the catheter is made much more accurate with the rotating tracking method and positioning of the catheter 3 in regard to an artery 30 and the plaque build-up 31 therein can be detected reliably and accurately.

Figure 4:
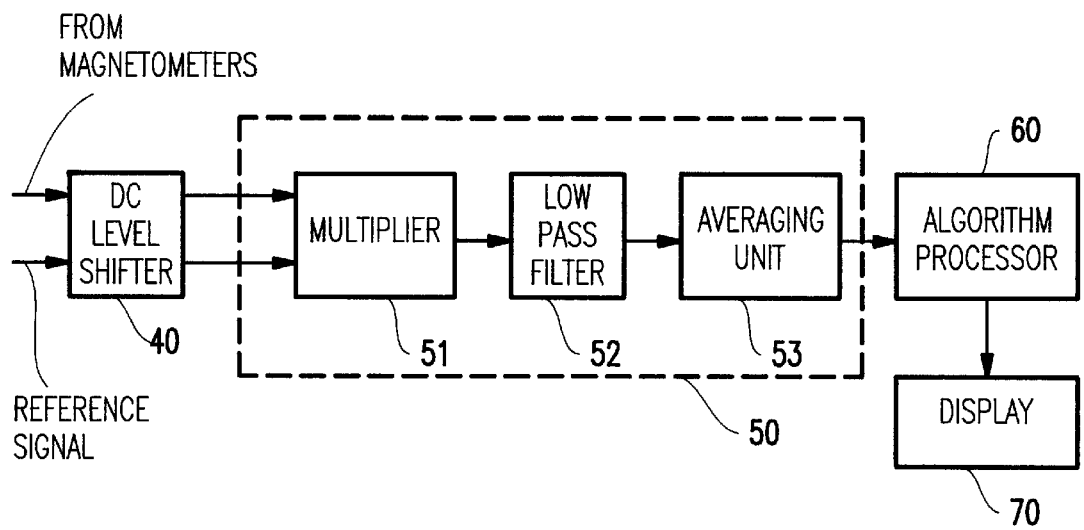
FIG. 4 illustrates a schematic digital lock-in for a computer 8 according to the present invention.

As shown in FIG. 4, the architecture of the computer 8 preferably comprises a direct current (DC) level shifter (subtractor) 40 to reduce the offset from zero of the average magnetic field, a digital lock-in unit 50 (preferably approximated in software for each of the input channels), and an algorithm processor 60 for performing the inventive algorithm, and specifically the inversion method discussed below, to select/provide a result. It is noted that, while the digital lock-in unit 50 preferably is approximated in software according to the present invention, the digital lock-in unit alternatively could be provided in hardware as would be known by one of ordinary skill in the art taking the present invention as a whole.

The digital lock-in is achieved by recording a reference signal from the rotating magnet synchronously with the rotating magnet 2. The signals from the magnetometers and the reference signals are input to the DC level shifter 40, as mentioned above, and then outputs are provided to a multiplier 51 of the digital lock-in 50.

An output from the multiplier is provided to a low pass filter 52 and filtered. Thereafter, an averaging unit 53 averages the outputs from the low pass filter 52, and provides an output. Typically, averaging unit 53 will provide 6–12 outputs (e.g., 3/magnetometer) depending upon the number of magnetometers. The outputs from the averaging unit 53 represents an estimate of the magnetic field from the respective magnets 2.

Thereafter, the outputs are input to the algorithm processor 60 which selects a result based on an inversion method, as discussed below with reference to FIG. 5. The result of the processor 60 is output to a display (e.g., cathode ray tube (CRT) monitor, printer, etc.) 70, if desired. It is noted that the display 70 does not constitute a component of the architecture of the computer 8.

Figure 5:
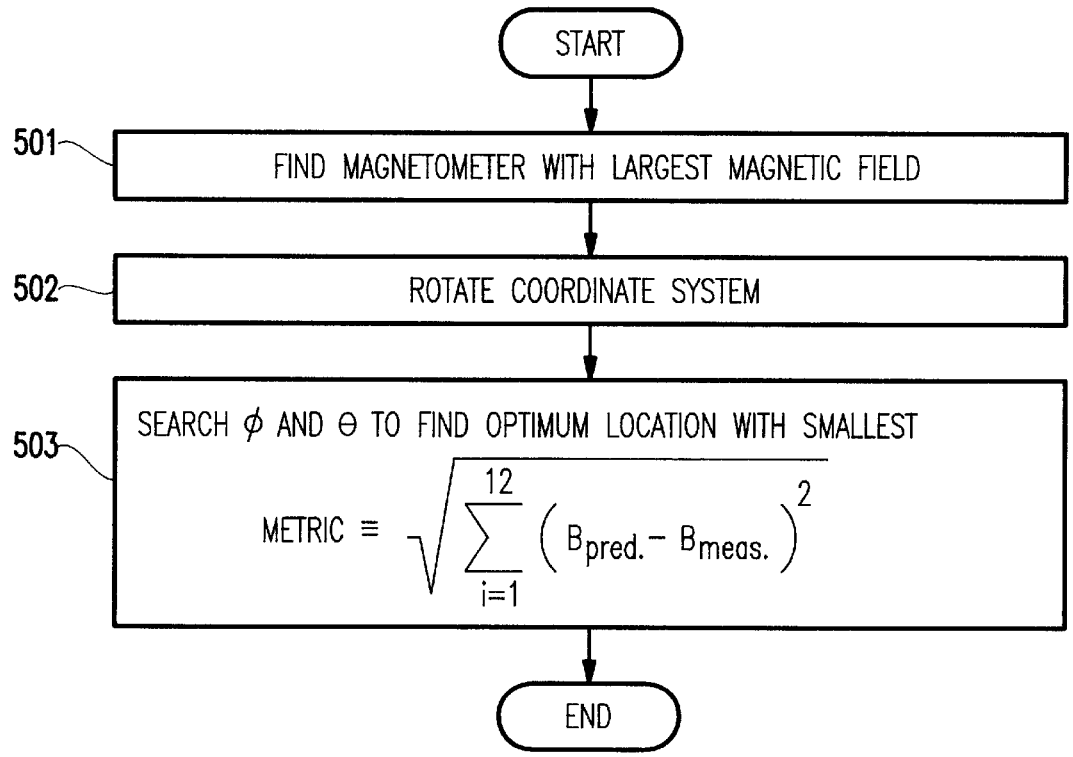
FIG. 5 is a flowchart of the steps of the process (e.g., an inversion method) for tracking the object in a body according to the present invention.

Referring now to FIG. 5, the inversion method performed by the algorithm processor 60 is described.

First, in step 501, the magnetometer with the largest magnetic field is found based on the values (e.g., 6 to 12 values) provided by the averaging unit 53. Such a process can be performed by comparing each of the values to one another and selecting the largest value, and storing the same.

Then, in step 502, the coordinate system is rotated so that the vector field lies in two direction for that vector (e.g., see the coordinate system of FIG. 1B). Using polar coordinates, only the φ and θ values are unknown.

Finally, in step 503, the φ and θ values are iteratively searched to find the best location. The best location will be the value with the smallest "metric" (e.g., smallest deviation between the predicted field and the measured field). Thus, the metric represents the "goodness of fit". Specifically, to find the "metric", the following equation is used:

$$\text{metric} \equiv \sqrt{\Sigma^{\cap\|}} (B_{L\oplus \supset c} - B_{\_/\supset <\ominus})^{\|}$$

The operation and tracking algorithm used by the computer 8 are described below.

In operation, the computer 8 (e.g., multiplier 51) multiplies the input signal of each of the magnetic sensors 4 by a reference signal from the rotating magnet 2 to produce a dc level which corresponds to the average magnetic field for that sensor 4 at the rotational frequency. This concept is exactly that of a lock-in implemented digitally.

Thereafter, the output of the digital lock-in can be used with the inversion algorithm (e.g., inversion method), to convert the measured magnetic fields into the position of the magnet 2.

Using the values of the magnetic fields at the measurement positions, the computer inversion algorithm converts the magnetic field values into a value representing the position of the magnet 2.

Hereinbelow, one cycle of the operation of attaching the magnet to the catheter 3, insertion of the catheter into the body, and then taking a measurement of the position of the catheter, is described.

The operation of the system is quite simple. First, the magnet is attached to the catheter, and then the catheter is placed into the human body. The catheter is normally rotated in order to make an ultrasonic measurement.

Then, the sensor platform holding the sensors 4 is placed near the body, and, by using the above described electronics and algorithm, the position of the rotating magnet, and hence the tip of the sensor, can be determined.

It is noted that, while such a measurement above may be made with the magnet affixed directly to the catheter, the technique according to the present invention works significantly better for catheters which allow the magnet to be attached to a rotating flexible shaft 9 within the catheter 3. Such catheters 3 are typically used to image ultrasonically the insides of blood vessels and arteries around the heart or in the urinary track. Such rotation is made possible, for example, by the motor 20 mentioned above.

As mentioned above, the three-dimensional imaging provided by the rotating magnet tracking of the present invention is highly accurate as compared to the two-dimensional imaging of the conventional techniques.

Thus, rotating magnet tracking is advantageous in that it inexpensively provides instantaneous and exact positional information of the location of the catheter 3. Such instantaneous and exact positional location is obtained without the need for an accurate dc measurement of the magnetic field of the hospital room before the catheter is introduced, as in a non-rotating source. Additionally, the rotating source tracking can be performed easily in an ordinary hospital environment.

ADVANTAGES OF THE PRESENT INVENTION

With the invention, costs are minimized since an extremely small rare earth magnet is positioned on a tip of a catheter which is an inexpensive and minimal alteration of the catheter.

Further, the reliability and accuracy of the measurement are high, as compared to the conventional systems.

While the invention has been described in terms of a single preferred embodiment, those skilled in the art will recognize that the invention can be practiced with modification within the spirit and scope of the appended claims.

Having thus described my invention, what I claim as new and desire to secure by Letters Patent is as follows:

1. A method of tracking an object within a volume, the method comprising steps of:
   coupling a rotating permanent magnet to said object;
   measuring magnetic fields produced by the rotating permanent magnet remotely or on the surface of or exterior to the volume, to produce measurements; and
   based on said measurements, determining a position and an orientation of the rotating permanent magnet and a position and orientation of said object to which said permanent magnet is coupled comprising:
      inputting said measurements to a processor, said measurements comprising signals representing values of the magnetic fields;
      filtering said signals to produce filtered signals;
      digitizing said filtered signals;
      recording a reference signal from the rotating permanent magnet synchronously with the rotating magnetic dipole;
      performing a direct current (DC) level shift of said digitized signals and the reference signal to reduce an offset from zero of an average magnetic field and produced a level-shifted value; and
      performing a digital lock-in operation based on said level-shifted value.

2. The method according to claim 1, wherein said digital lock-in operation comprises:
   multiplying each of said level-shifted values by a reference signal from the rotating permanent magnet to produce a DC level which corresponds to the average magnetic field for a respective sensor at a rotational frequency to produce multiplied values;
   filtering said multiplied values by a low pass filter; and
   averaging said multiplied values having been filtered to provide average outputs, said average outputs representing estimates of the magnetic fields.

3. The method according to claim 2, further comprising the step of processing to select a result, said step of processing comprising:
   performing an inversion method, said inversion method comprising:
      based on said multiplied values having been filtered, identifying a magnetic sensor having a largest magnetic field;
      rotating a coordinate system of the magnetic sensor having the largest magnetic field such that a vector field thereof lies in two directions using polar coordinates, iteratively searching for a combination of φ and Θ values which provide a smallest deviation between a predicted magnetic field and a measured magnetic field so to convert the magnetic fields into a position of the rotating permanent magnet.

4. The method according to claim 3, further comprising:
   displaying said result on a display.

5. A system for tracking an object in a volume, comprising:
   a rotating permanent magnet coupled to said object;
   at least two detectors for measuring magnetic fields exterior to the volume produced by said rotating permanent magnet, to produce measurements;

a determining unit for determining, based on said measurements, a position of the permanent magnet and a position of said object to which said permanent magnet is coupled;

a bandpass filter for filtering outputs from said at least two detectors, thereby providing a band pass around a rotational frequency of the permanent magnet, a filter being provided corresponding to each said at least two detectors; and an analog-to-digital (A/D) converter for converting filtered outputs from said filter to digital values representing the magnetic fields, said digital values being inputted into said determining unit, said determining unit comprising a computer.

6. The system according to claim 5, further comprising:

a motor for rotating said magnet, and for providing an alternating current (AC) reference synchronization signal to said A/D converter.

7. The system according to claim 6, further comprising:

a rotating shaft coupled to the object.

8. A system for tracking an object in a volume, comprising:

a rotating permanent magnet coupled to said object;

a detector for measuring magnetic fields exterior to the volume produced by said rotating permanent magnet, to produce measurements; and a determining unit for determining, based on said measurements, a position of the permanent magnet and a position of said object to which said permanent magnet is coupled comprising:

means for recording a reference signal from the rotating permanent magnet synchronously with the rotating permanent magnet;

a direct current (DC) level shifter for shifting a level of said digitized signals and the reference signal, to reduce an offset from zero of an average magnetic field and produced a level-shifted value; and a digital lock-in unit for performing a digital lock-in operation based on said level-shifted value.

9. The system according to claim 8, wherein said digital lock-in unit comprises:

a multiplier for multiplying each of said level-shifted values by a reference signal from the rotating permanent magnet to produce a DC level which corresponds to the average magnetic field for a respective sensor at a rotational frequency, to produce multiplied values;

a low pass filter for filtering said multiplied values; and an averaging unit for averaging said multiplied values having been filtered to provide average outputs, said average outputs representing estimates of the magnetic fields.

10. The system according to claim 9, further comprising a processor for processing to select a result, said processor including:

means, based on said multiplied values having been filtered, for identifying a detector detecting a largest magnetic field;

means for rotating a coordinate system of the detector detecting the largest magnetic field such that a vector field thereof lies in two directions; and means, by using polar coordinates, for iteratively searching for a combination of $\phi$ and $\Theta$ values which provide a smallest deviation between a predicted magnetic field and a measured magnetic field, so as to convert the magnetic fields into a position of the rotating permanent magnet.

* * * * *